（12） United States Patent
Venkatesan et al.

(10) Patent No.: US 9,421,377 B2
(45) Date of Patent: Aug. 23, 2016

(54) APPARATUS, METHOD AND SYSTEM FOR CLOSED-LOOP NEUROSTIMULATION

(71) Applicant: PACESETTER, INC., Sylmar, CA (US)

(72) Inventors: Lalit Venkatesan, McKinney, TX (US); Stuart Rosenberg, Castaic, CA (US)

(73) Assignee: PACESETTER, INC., Sylmar, CA (US)

( * ) Notice: Subject to any disclaimer, the term of this patent is extended or adjusted under 35 U.S.C. 154(b) by 141 days.

(21) Appl. No.: 14/109,589

(22) Filed: Dec. 17, 2013

(65) Prior Publication Data

US 2015/0165206 A1    Jun. 18, 2015

(51) Int. Cl.
*A61N 1/00*  (2006.01)
*A61N 1/36*  (2006.01)
*A61N 1/05*  (2006.01)

(52) U.S. Cl.
CPC .......... *A61N 1/36139* (2013.01); *A61N 1/0531* (2013.01)

(58) Field of Classification Search
CPC ........... A61N 1/36025; A61N 1/36139; A61N 1/0534
USPC ..................................................... 607/45, 62
See application file for complete search history.

(56) References Cited

U.S. PATENT DOCUMENTS

| | | | |
|---|---|---|---|
| 7,890,185 B2* | 2/2011 | Cohen ................ | A61N 1/36007 607/118 |
| 7,917,221 B2 | 3/2011 | Tass | |
| 8,280,514 B2 | 10/2012 | Lozano et al. | |
| 8,412,334 B2 | 4/2013 | Whitehurst et al. | |
| 2004/0133248 A1* | 7/2004 | Frei .......................... | A61N 2/00 607/45 |
| 2007/0027499 A1* | 2/2007 | Maschino .......... | A61N 1/36096 607/45 |
| 2009/0149898 A1* | 6/2009 | Hulvershorn ...... | A61N 1/36082 607/3 |
| 2012/0271374 A1* | 10/2012 | Nelson ............... | A61N 1/36082 607/45 |

* cited by examiner

*Primary Examiner* — Amanda Patton
*Assistant Examiner* — Philip C Edwards

(57) ABSTRACT

The present disclosure provides systems and methods utilizing a closed-loop neurostimulation apparatus. The apparatus includes at least one sensing electrode that monitors neurological activity of a subject and at least one stimulating electrode that applies stimulation pulses to the subject. An internal pulse generator is coupled to the at least one sensing electrode and the at least one stimulating electrode. The internal pulse generator causes the at least one stimulating electrode to apply stimulating pulses based at least in part on the monitored neurological activity.

14 Claims, 7 Drawing Sheets

APPARATUS, METHOD AND SYSTEM FOR CLOSED-LOOP NEUROSTIMULATION

FIELD OF THE DISCLOSURE

The present disclosure relates generally to neurostimulation methods, systems, and more particularly to an apparatus that applies stimulation via at least one stimulating electrode based on signals monitored by at least one sensing electrode.

BACKGROUND ART

Neurostimulation is a treatment method utilized for managing the disabilities associated with pain, movement disorders such as Parkinson's Disease (PD), dystonia, and essential tremor, and also a number of psychological disorders such as depression, mood, anxiety, addiction, and obsessive compulsive disorders. Closed-loop neurostimulation systems deliver the stimulation and modify stimulation parameters based on feedback. Closed-loop systems may reduce power consumption of an internal pulse generator (IPG), decreasing the need to recharge a battery, and increasing battery life. Further, closed-loop systems may be more efficacious in improving symptoms associated with the condition being treated.

Traditional closed-loop systems include incorporating sensors in a stimulating electrode and modulating the stimulation applied by the stimulating electrode based on signals detected by the sensors. In addition to sensing signals in a target area, however, other areas may be reflective of abnormal neural activity associated with a disease condition. Further, electrode polarization from stimulation may interfere with the ability to accurately monitor activity at the stimulating electrode.

BRIEF SUMMARY OF THE DISCLOSURE

In one embodiment, the present disclosure is directed to a neurostimulation apparatus. The neurostimulation apparatus comprises at least one sensing electrode, at least one stimulating electrode, and an internal pulse generator coupled to the at least one sensing electrode and the at least one stimulating electrode. The internal pulse generator is configured to cause the at least one stimulating electrode to apply at least one stimulation pulse based at least in part on neurological activity monitored by the at least one sensing electrode.

In another embodiment, the present disclosure is directed to an internal pulse generator. The internal pulse generator is configured to receive signals from at least one sensing electrode, the received signals indicative of neurological activity monitored by the at least one sensing electrode, generate at least one stimulation pulse based at least in part on the monitored neurological activity, and transmit the at least one stimulation pulse to at least one stimulating electrode.

In another embodiment, the present disclosure is directed to a method for applying neurostimulation to a subject. The method comprises monitoring neurological activity using at least one sensing electrode, receiving, at an internal pulse generator, signals from the at least one sensing electrode that are indicative of the monitored neurological activity, and applying, using at least one stimulating electrode coupled to the internal pulse generator, at least one stimulation pulse based at least in part on the monitored neurological activity.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
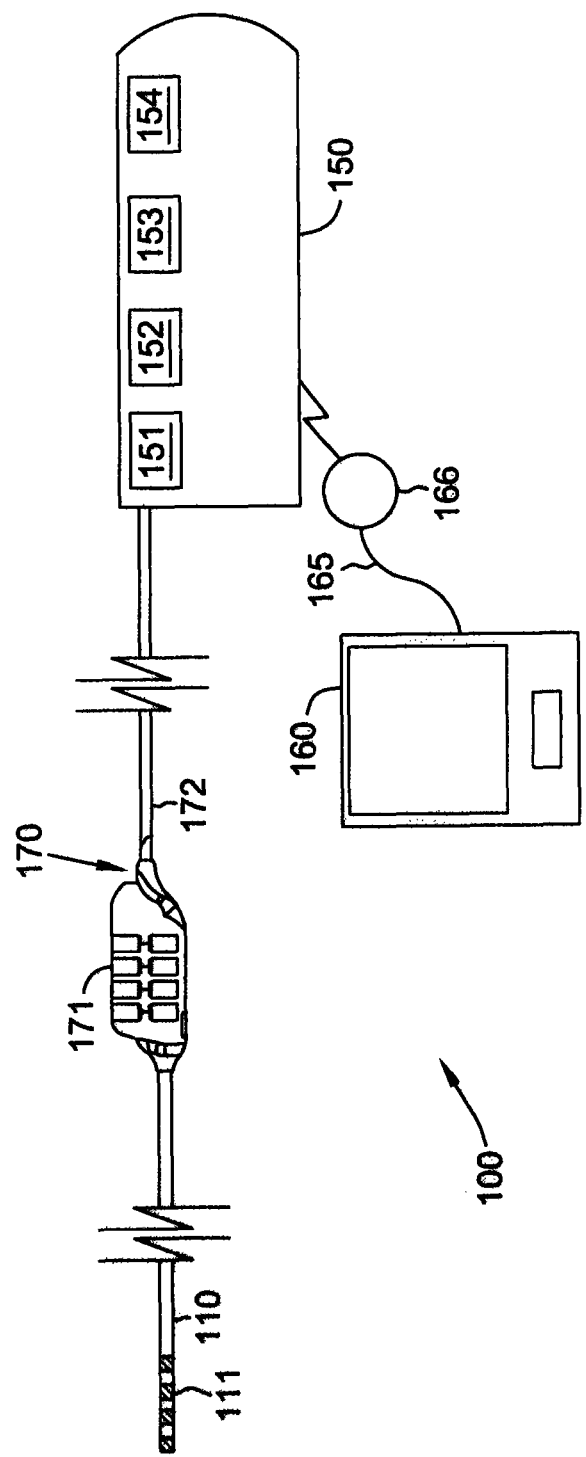
FIG. 1 is a schematic view of one embodiment of a stimulation system.

The present disclosure provides systems and methods utilizing a closed-loop neurostimulation apparatus. The neurostimulation apparatus includes at least one sensing electrode that monitors neurological activity of a subject and at least one stimulating electrode that applies stimulation pulses to the subject. An internal pulse generator is coupled to the at least one sensing electrode and the at least one stimulating electrode. The internal pulse generator causes the at least one stimulating electrode to apply stimulating pulses based at least in part on the monitored neurological activity. By monitoring neurological activity in a first region, and applying stimulation in a second region, the present disclosure provides a neurostimulation apparatus that accurately monitors neurological activity and selectively applies stimulation accordingly.

Neurostimulation systems are devices that generate electrical pulses and deliver the pulses to nerve tissue of a patient to treat a variety of disorders. Spinal cord stimulation (SCS) is the most common type of neurostimulation within the broader field of neuromodulation. In SCS, electrical pulses are delivered to nerve tissue in the spine typically for the purpose of chronic pain control. While a precise understanding of the interaction between the applied electrical energy and the nervous tissue is not fully appreciated, it is known that application of an electrical field to spinal nervous tissue can effectively mask certain types of pain transmitted from regions of the body associated with the stimulated nerve tissue. Specifically, applying electrical energy to the spinal cord associated with regions of the body afflicted with chronic pain can induce "paresthesia" (a subjective sensation of numbness or tingling) in the afflicted bodily regions. Thereby, paresthesia can effectively mask the transmission of non-acute pain sensations to the brain.

SCS systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals (also electrically coupled to the wire conductors) that are adapted to receive electrical pulses. The distal end of a respective stimulation lead is implanted within the epidural space to deliver the electrical pulses to the appropriate nerve tissue within the spinal cord that corresponds to the dermatome(s) in which the patient experiences chronic pain. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

The pulse generator is typically implemented using a metallic housing that encloses circuitry for generating the electrical pulses, control circuitry, communication circuitry, a rechargeable battery, etc. The pulse generating circuitry is coupled to one or more stimulation leads through electrical connections provided in a "header" of the pulse generator. Specifically, feedthrough wires typically exit the metallic housing and enter into a header structure of a moldable material. Within the header structure, the feedthrough wires are electrically coupled to annular electrical connectors. The header structure holds the annular connectors in a fixed arrangement that corresponds to the arrangement of terminals on a stimulation lead.

Peripheral nerve field stimulation (PNFS) is another form of neuromodulation. The basic devices employed for PNFS are similar to the devices employed for SCS including pulse generators and stimulation leads. In PNFS, the stimulation leads are placed in subcutaneous tissue (hypodermis) in the area in which the patient experiences pain. Electrical stimulation is applied to nerve fibers in the painful area. PNFS has been suggested as a therapy for a variety of conditions such as migraine, occipital neuralgia, trigeminal neuralgia, lower back pain, chronic abdominal pain, chronic pain in the extremities, and other conditions.

Referring now to the drawings, and in particular to FIG. 1, a stimulation system is indicated generally at 100. Stimulation system 100 generates electrical pulses for application to tissue of a patient, or subject, according to one embodiment. System 100 includes an implantable pulse generator 150 that is adapted to generate electrical pulses for application to tissue of a patient. Implantable pulse generator 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of pulse generator 150 for execution by the microcontroller or processor to control the various components of the device.

Pulse generator 150 may comprise one or more attached extension components 170 or be connected to one or more separate extension components 170. Alternatively, one or more stimulation leads 110 may be connected directly to pulse generator 150. Within pulse generator 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from pulse generator 150 and conducted through the conductors of lead body 172 are provided to stimulation lead 110. The pulses are then conducted through the conductors of lead 110 and applied to tissue of a patient via electrodes 111. Any suitable known or later developed design may be employed for connector portion 171.

For implementation of the components within pulse generator 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 20060170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within pulse generator 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of lead 110 to its distal end. The conductors electrically couple a plurality of electrodes 111 to a plurality of terminals (not shown) of lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

Figure 2A:
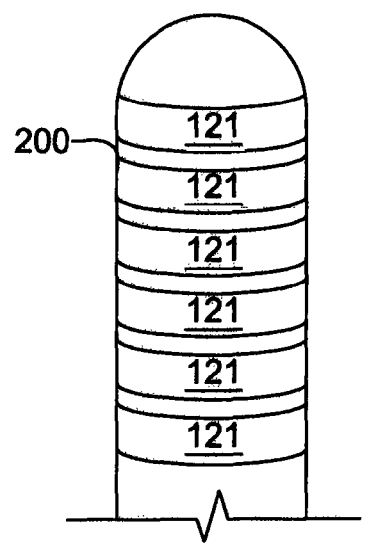
FIGS. 2A-2C are schematic views of stimulation portions that may be used with stimulation system of FIG. 1.
Figure 2B:
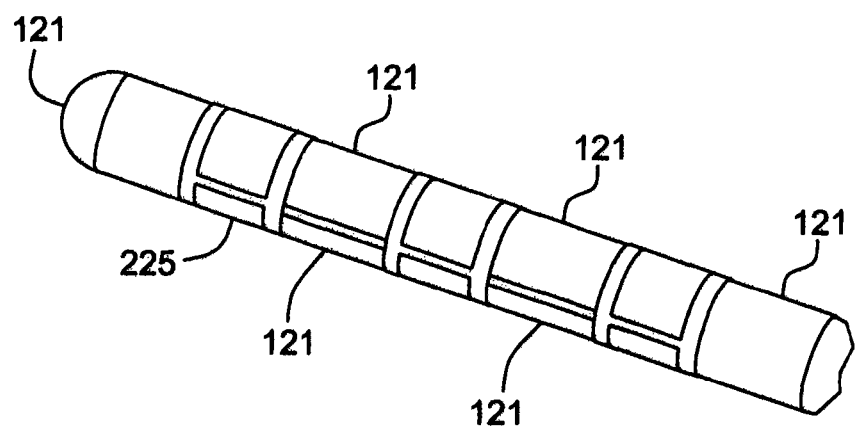
Figure 2C:
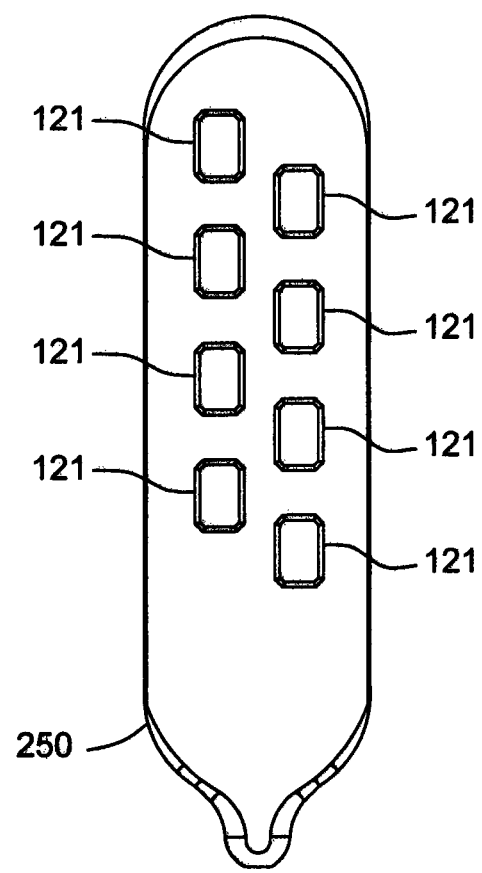

FIGS. 2A-2C respectively depict stimulation portions 200, 225, and 250 for inclusion at the distal end of lead 110. Stimulation portion 200 depicts a conventional stimulation portion of a "percutaneous" lead with multiple ring electrodes. Stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Patent Publication No. 2010072657, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Controller device 160 may be implemented to recharge battery 153 of pulse generator 150 (although a separate recharging device could alternatively be employed). A "wand" 165 may be electrically connected to controller device through suitable electrical connectors (not shown). The electrical connectors are electrically connected to coil 166 (the "primary" coil) at the distal end of wand 165 through respective wires (not shown). Typically, coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller 160 generates an AC-signal to drive current through coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery of generator 150. The charging circuitry may also communicate status messages to controller 160 during charging operations using pulse-loading or any other suitable technique. For example, controller 160 may communicate the coupling status, charging status, charge completion status, etc.

External controller device 160 is also a device that permits the operations of pulse generator 150 to be controlled by user after pulse generator 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with IPG 150.

Controller device 160 preferably provides one or more user interfaces to allow the user to operate pulse generator 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimsets during execution of program), etc. IPG 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 01/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Example commercially available neurostimulation systems include the EON MINI™ pulse generator and RAPID PROGRAMMER™ device from St. Jude Medical, Inc. (Plano, Tex.). Example commercially available stimulation leads include the QUATTRODE™, OCTRODE™, AXXESS™, LAMITRODE™, TRIPOLE™, EXCLAIM™, and PENTA™ stimulation leads from St. Jude Medical, Inc.

Figure 3:
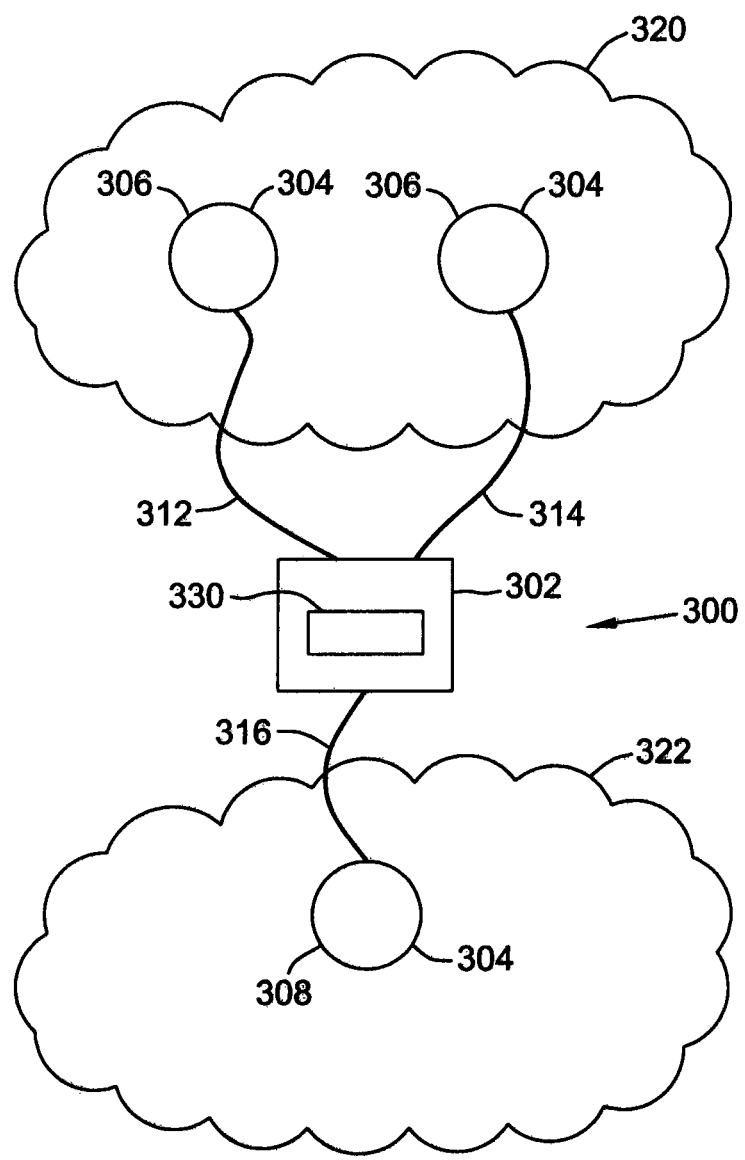
FIG. 3 is a schematic view of one embodiment of a neurostimulation apparatus including an internal pulse generator, at least one sensing electrode, and at least one stimulating electrode.

In FIG. 3, an implantable neurostimulation apparatus is indicated generally at 300. Apparatus 300 includes an internal pulse generator (IPG) 302 electrically coupled to a plurality of electrodes 304. In the illustrated embodiment, apparatus 300 includes two sensing electrodes 306 and one stimulating electrode 308. Alternatively, in other suitable embodiments, apparatus 300 may include any number of sensing and stimulating electrodes 306 and 308 that enables apparatus 300 to function as described herein. For example, in one embodiment, apparatus 300 includes two monopolar sensing electrodes 306 implanted on either side of a subject's brain. In another embodiment, apparatus 300 includes a single bipolar sensing electrode 306.

Sensing electrodes 306 are electrically coupled to IPG 302 by first and second leads 312 and 314, and stimulating electrode 308 is electrically coupled to IPG 302 by a third lead 316. IPG 302 generates and supplies one or more electrical stimulation pulses to stimulating electrode 308.

Sensing electrodes 306 are implanted in a first region 320 of the subject's nervous system, and stimulating electrode 308 is implanted in a second region 322 of the subject's nervous system. In the illustrated embodiment, both sensing electrodes 306 are located in the same region 320. Alternatively, sensing electrodes 306 may be implanted in different regions of the subject's nervous system. Notably, in the illustrated embodiment, first region 320 is different than second region 322, such that sensing electrodes 306 do not operate at the same location as stimulating electrode 308. If sensing were performed at the same location as stimulation, blanking requirements and electrode polarization from stimulation may limit the available window for sensing signals of interest. Sensing in a first region 320 that is remote from second region 322 avoids this phenomenon.

To monitor activity, sensing electrodes 306 may measure local field potentials and/or utilize electrocorticography. Further, sensing electrodes 306 may detect magnitude, latency, spectral power, and/or oscillations associated with such signals.

Electrodes 304 may by implanted in an epidural surface, subdural surface, or a surface of the subject's skull. Exemplary regions 320 and 322 where sensing and stimulating electrodes 306 and 308 may be implanted are described in detail herein. For example, sensing electrodes 306 may be implanted on the subdural or epidural surface of the cerebral cortex, and stimulating electrode 308 may be implanted in a sub-cortical structure (e.g., in the subthalamic nucleus for treating Parkinson's disease) or on the epidural surface (e.g., for treatment of pain). IPG 302 may be implanted, for example, on the skull of the subject.

Apparatus 300 functions as a closed-loop system in which stimulating electrode 308 applies stimulation (i.e., electrical pulses) to second region 322 based on activity monitored by sensing electrodes 306 in first region 320. Specifically, IPG 302 receives signals from sensing electrodes 306 indicative of activity monitored by sensing electrodes 306, and causes stimulating electrode 308 to deliver one or more electrical pulses based at least in part on the received signals. As stimulation is selectively provided instead of continuously, the closed-loop design generally has lower power consumption than traditional neurostimulation systems that employ continuous stimulation. Further, the progression of a disability or disease state may be monitored using apparatus 300, and the effectiveness of the current stimulation treatment may be determined, as described herein. To facilitate processing signals from sensing electrodes 306 and controlling stimulating electrode 308, in the illustrated embodiment, IPG 302 includes a computing device 330.

Figure 4:
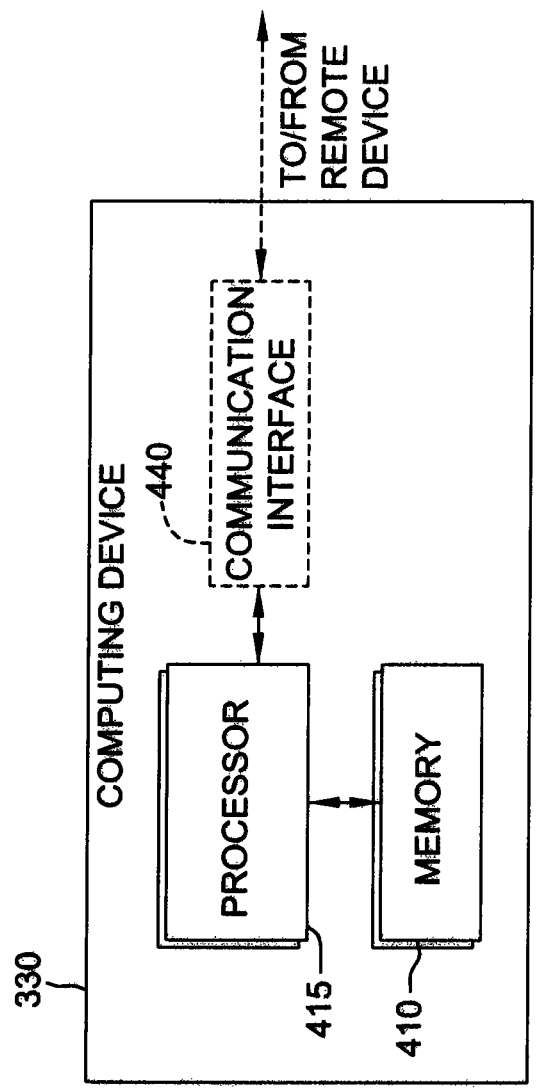
FIG. 4 is a block diagram of one embodiment of a computing device that may be used with the neurostimulation apparatus of FIG. 3.

FIG. 4 is a block diagram of one embodiment of computing device 330 that may be used with IPG 302 (shown in FIG. 3). Computing device 330 includes at least one memory device 410 and a processor 415 that is coupled to memory device 410 for executing instructions. In some embodiments, executable instructions are stored in memory device 410. In the illustrated embodiment, computing device 330, and by extension IPG 302, performs one or more operations described herein by programming processor 415. For example, processor 415 may be programmed by encoding an operation as one or more executable instructions and by providing the executable instructions in memory device 410.

Processor 415 may include one or more processing units (e.g., in a multi-core configuration). Further, processor 415 may be implemented using one or more heterogeneous processor systems in which a main processor is present with secondary processors on a single chip. In another illustrative example, processor 415 may be a symmetric multi-processor system containing multiple processors of the same type. Further, processor 415 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein. In the illustrated embodiment, processor 415 processes signals received from sensing electrodes 306 and controls stimulating electrode 308, as described herein. In the illustrated embodiment, processor 415 receives signals from sensing electrodes 306 and controls IPG 302 to deliver one or more pulses to stimulating electrode 308 based at least in part on the received signals.

In the illustrated embodiment, memory device 410 is one or more devices that enable information such as executable instructions and/or other data to be stored and retrieved. Memory device 410 may include one or more computer readable media, such as, without limitation, dynamic random access memory (DRAM), static random access memory (SRAM), a solid state disk, and/or a hard disk. Memory device 410 may be configured to store, without limitation, application source code, application object code, source code portions of interest, object code portions of interest, configuration data, execution events and/or any other type of data. In some embodiments, memory device 410 includes template neural signatures associated with predetermined disabilities or disease conditions. Using processor 415, signals sensed by sensing electrodes 306 may be compared with the template neural signatures (e.g., using pattern matching and/or prediction algorithms) to identify a predetermined disability or disease condition and modify stimulation accordingly.

Computing device 330, in the illustrated embodiment, includes a communication interface 440 coupled to processor 415. Communication interface 440 communicates with one or more remote devices, such as a clinician or patient programmer (not shown in FIG. 4). To communicate with remote devices, communication interface 440 may include, for example, a wired network adapter, a wireless network adapter, a radio-frequency (RF) adapter, and/or a mobile telecommunications adapter.

Apparatus 300 may be used to manage pain, treatment resistant depression, and/or disabilities associated with movement disorders such as Parkinson's disease, dystonia, and essential tremor. Stimulation parameters pertinent to the particular disability or disease condition to be managed are programmed on processor 415.

Sensing electrodes 306 are implanted on the subdural or epidural surface of the cerebral cortex to monitor cortical signals in the exemplary embodiment. In other embodiments, sensing electrodes 306 may be implanted on, for example, the spinal cord or the skull of the subject. Monitoring certain cortical signals may be utilized to predict the effectiveness of stimulation applied by stimulating electrode 308 and to monitor symptoms associated with the particular disability or disease condition. For example, rhythmic oscillation or abnormal cortical activity has been observed in movement related-disorders (e.g., Parkinson's disease, dystonia, epilepsy) and psychological disorders (e.g., depression). Further, activity monitored by sensing electrodes 306 in a cortical region may serve as an indication of the effectiveness of deep brain stimulation (DBS) applied by stimulating electrode 308 in a downstream sub-cortical region. Accordingly, cortical signals monitored by sensing electrodes 306 are used to automatically adjust stimulation parameters that control operation of stimulating electrode 308.

In one embodiment, stimulating electrode 308 is implanted in the subthalamic nucleus (STN) for delivering stimulation therapy to treat Parkinson's disease or other movement disorders, and sensing electrodes 306 are implanted subdurally or epidurally on the region of the primary motor cortex that controls movement of the hands. To facilitate improving sensing, sensing electrodes 306 may be separated by, for example, at least 5 millimeters (mm). By using a plurality of sensing electrodes 306 at some distance from one another, different regions of activity can be measured. Further, in addition to including sensing electrodes 306 in the primary motor cortex, additional sensing electrodes 306 may be included in other areas associated with movement (e.g., the pre-motor cortex, the supplementary motor areas, and/or sensorimotor areas).

In this embodiment, sensing electrodes 306 are configured to detect rhythmic oscillations in the primary motor cortex that reflect abnormal synchronized activity in the STN. In response to detecting these rhythmic oscillations, IPG supplies stimulation pulses to stimulating electrode 308. The stimulation may continue until a short time (e.g., a few seconds) after cortical signals monitored by sensing electrodes 306 indicate that the oscillations have subsided.

In another embodiment, which may be used to treat intentional tremor from Parkinson's disease, sensing electrodes 306 are placed over cortical regions that will be activated during planning, imitating, and observing movements (e.g., the pre-motor cortex, the supplementary motor areas, the primary somatosensory cortex, or the inferior parietal cortex). With sensing electrodes 306 implanted, the subject may be asked to move his or her hand in various directions and/or to imagine the same hand movements without actually moving. While the subject performs these tasks, associated cortical signals are monitored using sensing electrodes 306 and recorded, for example, using memory device 410.

Accordingly, cortical signals associated with planning and/or intent to move the hand are stored as templates. Subsequently, when IPG 302 receives signals from sensing electrodes 306 that match the stored templates, IPG 302 causes stimulating electrode 308 to apply pulses that allow the subject to move his or her hand without tremor.

In other embodiments, to treat psychological disorders (e.g., depression, mood, anxiety, addiction, and/or obsessive compulsion disorders), stimulating electrode 308 may be implanted at the subgenual cingulated, ventral capsule, nucleus accumbens, and/or medial forebrain bundle. Sensing electrodes 306 may be implanted in the medial frontal cortex, orbitofrontal cortex, and/or dorsolateral prefrontal cortex. To target both larger and more specific areas for sensing, in the exemplary embodiment, a plurality of sensing electrodes 306 are utilized.

Activity in the frontal cortical areas monitored by sensing electrodes 306 may be reflective of abnormal activity in the subcortical regions associated with psychological disorders. Accordingly, similar to the embodiments described above, when abnormal activity is detecting by sensing electrodes 306, IPG 302 causes stimulating electrode 308 to apply stimulation pulses. When abnormal activity subsides, stimulation is stopped.

In some embodiments, neurostimulation apparatus 300 provides advanced feedback beyond merely activating and deactivating stimulation based on activity monitored by sensing electrodes 306. That is, the number, frequency, pulse width, burst pattern, amplitude, and/or other parameters of the stimulation pulses may be manipulated based on signals monitored by sensing electrodes 306. Further, different stimulating electrodes 308 may be selectively activated and deactivated based on the monitored signals.

For example, in one embodiment, when oscillatory activity at a first frequency is detected by sensing electrodes 306, IPG 302 causes stimulating electrode 308 to apply pulses having a frequency slightly higher (e.g., 2-10 Hertz (Hz)) that the first frequency. Transmitting stimulating pulses at a slightly higher frequency facilitates interruption of pathologic oscillations in the targeted structures. In another example, an amplitude of the stimulation pulses may be gradually increased until cortical activity sensed using sensing electrodes 306 diminishes to a predetermined level.

In some embodiments, to facilitate effective stimulation, a latency between the activity sensed in first region 320 and the source activity in second region 322 is determined using a calibration procedure. For example, it may take from approximately 10 milliseconds (ms) to 300 ms for an oscillation in second region 322 to propagate to a detectable signal in first region 320.

Figure 5:
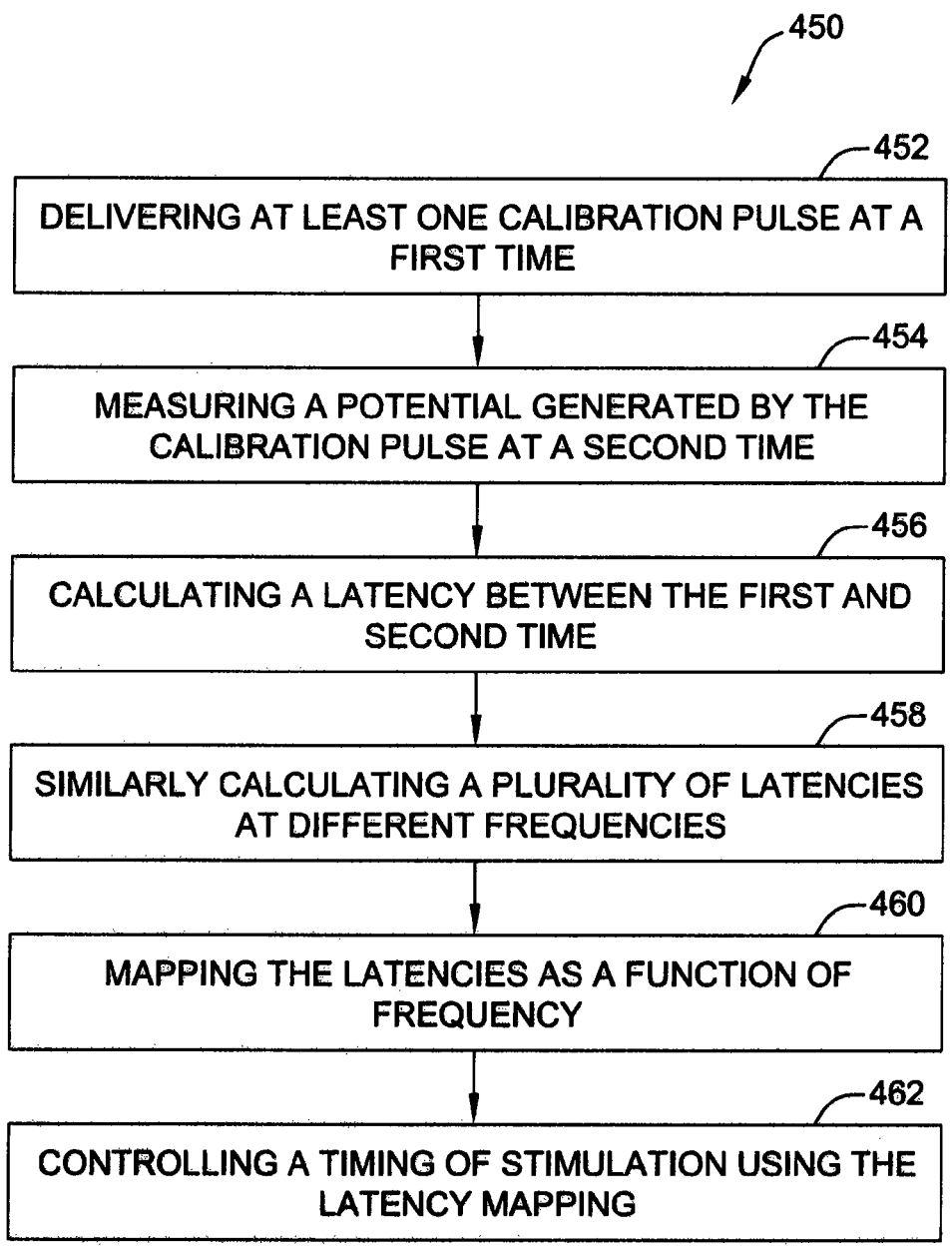
FIG. 5 is a flow chart of one embodiment of a method for performing a calibration procedure.

FIG. 5 is a flow chart of one embodiment of a method 450 for performing a calibration procedure. At block 452, at least one calibration pulse is delivered at a first time in second region 322 by stimulating electrode 308. The calibration pulse generates a potential, which is measured by sensing electrode 306 at a second time at block 454. At block 456, the time difference between the first time and the second time is calculated by, for example, processor 415 as the latency.

This may be repeated, at block 458, to calculate a plurality of latencies at several frequencies below, equal to, and above a primary oscillatory frequency (e.g., in a range from approximately 130 to 180 Hz). At block 460, the latencies are mapped as a function of frequency using, for example, processor 415. The mapping may be stored, for example, in memory device 410.

Using the latency mapping, at block 462, the timing of the stimulation can be precisely controlled to facilitate interrupting undesirable oscillatory activity. That is, when sensing electrode 306 detects oscillation in first region 320, processor 415 calculates the latency using the mapping, and uses the calculated latency to determine the timing of the oscillation as it is occurring in second region 322. Accordingly, stimulation can be precisely delivered at a vulnerable part of the oscillation, interrupting the oscillation with a relatively short, targeted pulse sequence.

Figure 6:
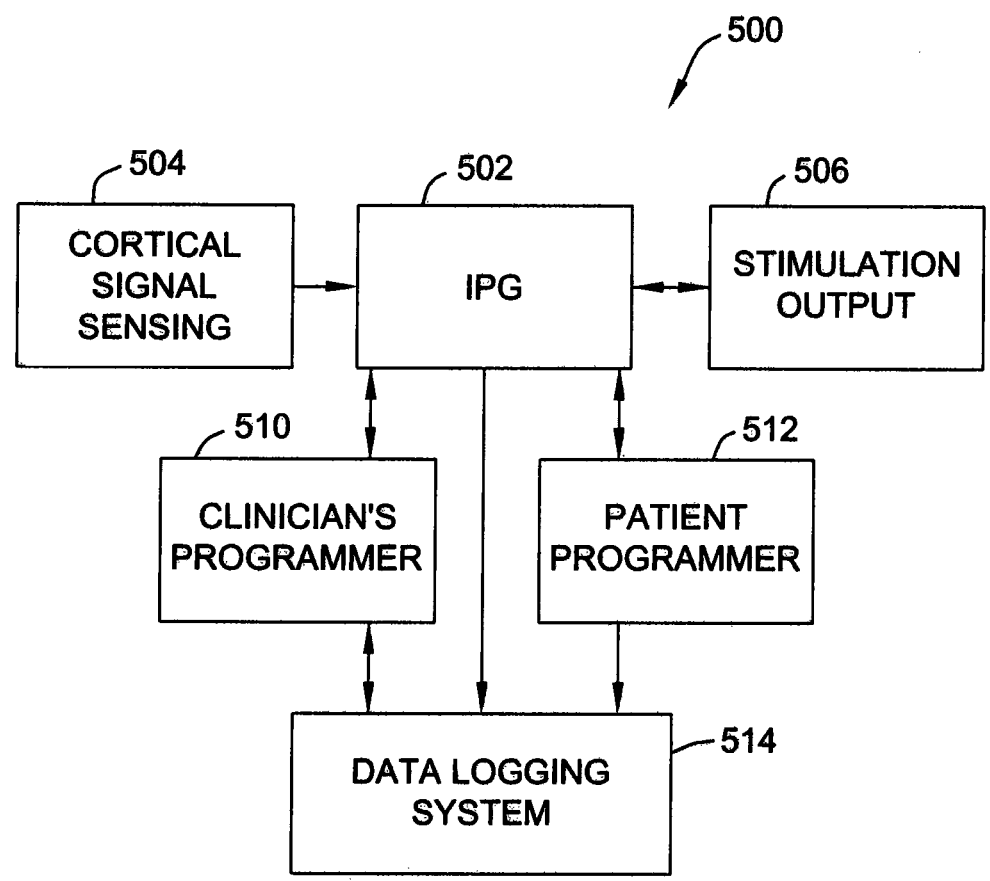
FIG. 6 is a block diagram of one embodiment of a neurostimulation system of the present disclosure.

FIG. 6 is a block diagram of one embodiment of a neurostimulation system 500. In the illustrated embodiment, system 500 includes an IPG 502, such as IPG 302 (shown in FIG. 3), a cortical signal sensing module 504 (i.e., sensing electrodes 306), and a stimulation output module 506 (i.e., stimulating electrode 308).

As shown in FIG. 6, IPG 502 is communicatively coupled to a clinician programmer 510, a patient programmer 512, and a data logging system 514. Further, clinician and patient programmers 510 and 512 are communicatively coupled to data logging system 514 in the illustrated embodiment. IPG 502, clinician programmer 510, patient programmer 512, and data logging system 514 may communicate with one another using RF signals, wireless, and/or any other communication protocol that enables system 500 to function as described herein. As described above, IPG 502, cortical signal sensing module 504, and stimulation output module 506 are implanted within the subject. However, clinician programmer 510, patient programmer 512, and data logging system 514 are computing devices that are typically external to the subject.

IPG 500 may transmit programming data and sensing data to data logging system 514 for storage. Clinician and patient programmers 510 and 512 may also transmit data to data logging system 514. In some embodiments, data logging system 514 is a cloud-based storage system. Alternatively, data logging system 514 may be any data storage architecture that enables system 500 to function as described herein.

Clinician and patient programmers 510 and 512 may also be used by a clinician and the subject, respectively, to program IPG 502. For example, programmers 510 and 512 may communicate with IPG 502 to modify stimulation applied by stimulating electrode 308. Accordingly, IPG 502 can be programmed to apply different stimulation parameters to the subject relatively easily. As such, programmers 510 and 512 may be utilized to provide different subjects with customized stimulation regimes.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A neurostimulation apparatus comprising:
   at least one sensing electrode implanted in a first region of a subject's nervous system;
   at least one stimulating electrode implanted in a second region of the subject's nervous system; and
   an internal pulse generator coupled to the at least one sensing electrode and the at least one stimulating electrode, the internal pulse generator configured to cause the at least one stimulating electrode apply at least one stimulation pulse based at least in part on neurological activity monitored by the at least one sensing electrode and wherein the second region is chosen such that the available window for the at least one sensing electrode to sense signals of the monitored neurological activity is not limited by blanking requirements and electrode polarization from the at least one stimulating electrode applying the at least one stimulation pulse at the first region;
   the internal pulse generator further configured to calculate a plurality of latencies, at different frequencies associated with the neurostimulation apparatus, wherein a latency is defined as a time difference between an application of a calibration pulse at a frequency by the at least one stimulating electrode and a detection of neurological activity indicative of the calibration pulse by the at least one sensing electrode, and mapping the latencies as a function of frequency, and the internal pulse generator further configured to control the timing of stimulation using the mapped latencies.

2. The neurostimulation apparatus of claim 1 wherein the at least one sensing electrode is implanted in a cortical region of a subject and the at least one stimulating electrode is implanted in a subcortical region of the subject.

3. The neurostimulation apparatus of claim 1, wherein the at internal pulse generator is configured to modify at least one of a frequency, pulse width, burst pattern, and amplitude of the at least one stimulation pulse based at least in part on the monitored neurological activity.

4. The neurostimulation apparatus of claim 1 wherein the internal pulse generator is configured to:
   receive signals from the at least one sensing electrode that are indicative of oscillation at a first frequency; and
   cause the at least one stimulating electrode to apply a plurality of stimulation pulses at a second frequency greater than the first frequency.

5. The neurostimulation apparatus of claim 1 wherein the internal pulse generator is configured to gradually increase an amplitude of a plurality of stimulation pulses applied by the at least one stimulating electrode until the monitored neurological activity decreases to a predetermined level.

6. The neurostimulation apparatus of claim 1 wherein the internal puke generator comprises a computing device comprising:
   a processor; and
   a memory device coupled to the processor.

7. An internal pulse generator configured to:
   receive signals from at least one sensing electrode, the at least one sensing electrode implanted in a first region of a subject, the received signals indicative of neurological activity monitored by the at least one sensing electrode;
   generate at least one stimulation pulse based at least in part on the monitored neurological activity: and
   transmit the at least one stimulation pulse to at least one stimulating electrode, the at least one stimulating electrode implanted in a second region of the subject, wherein the first region is chosen such that the available window for the at least one sensing electrode to sense signals of the monitored neurological activity is not limited by blanking requirements and electrode polarization from the at least one stimulating electrode applying the at least one stimulation pulse at the second region;
   calculate a plurality of latencies at different frequencies, wherein a latency defined as a time difference between application of a calibration pulse at a frequency by the at least one stimulating electrode and a detection of neurological activity indicative of the calibration pulse by the at least one sensing electrode, and mapping the latencies a function of frequency, and to control the timing of stimulation using the mapped latencies.

8. The internal pulse generator of claim 7 wherein the internal pulse generator is configured to modify at least one of a frequency, pulse width, burst pattern, and amplitude of the at least one stimulation pulse based at least in part on the monitored neurological activity.

9. The internal pulse generator of claim 7 wherein the internal pulse generator is configured to:
   receive signals from the at least one sensing electrode that are indicative of oscillation at a first frequency; and
   generate a plurality of stimulation pulses at a second frequency greater than the first frequency.

10. The internal pulse generator of claim 7 wherein the internal pulse generator is configured to gradually increase an amplitude of a plurality of stimulation pulses until the monitored neurological activity decreases to a predetermined level.

11. A method for applying neurostimulation to a subject, the method comprising:
    monitoring neurological activity using at least one sensing electrode, the at least one sensing electrode implanted in a first region of a subject;
    receiving, at an internal pulse generator, signals from the at least one sensing electrode that are indicative of the monitored neurological activity;
    applying, using at least one stimulating electrode coupled to the internal pulse generator, at least one stimulation pulse based at least in part on the monitored neurological activity, the at least one stimulating electrode implanted in a second region of the subject, wherein the first region is chosen such that the available window for the at least one sensing electrode to sense signals of the monitored neurological activity is not limited by blanking requirements and electrode polarization from the at least one stimulating electrode applying the at least one stimulation pulse at the second region;
    calculating a plurality of latencies at different frequencies, wherein a latency is; defined as a time difference between an application of a calibration pulse at a frequency by the at least one stimulating electrode and a detection of neurological activity indicative of the calibration pulse by the at least one sensing electrode;
    mapping the latencies as a function of frequency; and controlling the timing of stimulation using the mapped latencies.

12. The method of claim 11 further comprising:
implanting the at least one sensing electrode in a cortical region of a subject; and
implanting the at least one stimulating electrode in a sub-cortical region of the subject.

13. The method of claim 11 further comprising modifying at least one of a frequency, pulse width, burst pattern, and amplitude of the at least one stimulation pulse based at least in part on the monitored neurological activity.

14. The method of claim 11 further comprising gradually increasing an amplitude of a plurality of stimulation pulses applied by the at least one stimulating electrode unto the monitored neurological activity decreases to a predetermined level.

* * * * *